United States Patent [19]

Huettenrauch et al.

[11] Patent Number: 4,744,099
[45] Date of Patent: May 10, 1988

[54] X-RAY DIAGNOSTIC APPARATUS COMPRISING RADIATION FILTERS

[75] Inventors: Gerd Huettenrauch, Uttenreuth; Hans-Peter Seubert, Heroldsbach, both of Fed. Rep. of Germany

[73] Assignee: Siemens Aktiengesellschaft, Berlin and Munich, Fed. Rep. of Germany

[21] Appl. No.: 664,970

[22] Filed: Oct. 26, 1984

[30] Foreign Application Priority Data

Nov. 3, 1983 [DE] Fed. Rep. of Germany ....... 3339775

[51] Int. Cl.$^4$ .............................................. G21K 3/00
[52] U.S. Cl. .................................... 378/157; 378/156; 378/37; 378/95
[58] Field of Search ..................... 378/157, 156, 95, 37

[56] References Cited

U.S. PATENT DOCUMENTS

| | | | |
|---|---|---|---|
| 3,706,888 | 12/1972 | Wunsch | 378/157 |
| 3,976,889 | 8/1976 | Noske et al. | |
| 4,090,084 | 5/1978 | Epstein et al. | 378/37 |
| 4,403,337 | 9/1983 | Kleinman | 378/95 |

FOREIGN PATENT DOCUMENTS

| | | | |
|---|---|---|---|
| 0749087 | 11/1944 | Fed. Rep. of Germany | 378/95 |
| 2105259 | 8/1971 | Fed. Rep. of Germany | 378/156 |
| 1064486 | 12/1983 | U.S.S.R. | 378/157 |

Primary Examiner—Janice A. Howell
Assistant Examiner—David P. Porter

[57] ABSTRACT

A positioning control system controls the shifting of one of a plurality of radiation filters into the ray path. Transducers provide an electric density signal which is dependent upon the density of the examination subject. The control system has an electromotor activated by a control circuit to which the density signal is applied and which activates the motor corresponding to the respective density signal for the purpose of selection of the correct filter. The transducers may be coupled with a device physically acting in compression on a body part of the patient to be examined such that the degree of resistance of the body part to compression is sensed by the transducers as a measure of patient density.

4 Claims, 1 Drawing Sheet

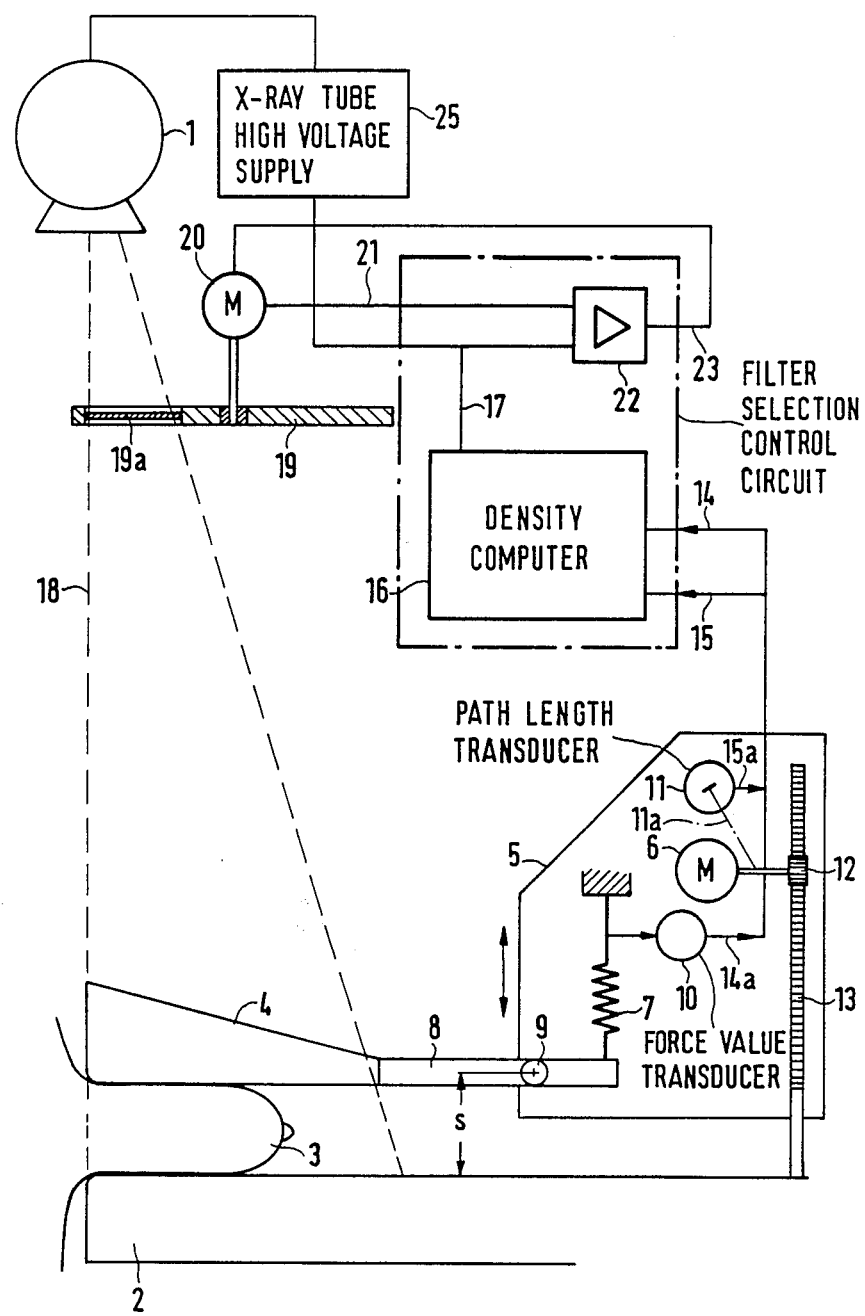

X-RAY DIAGNOSTIC APPARATUS COMPRISING RADIATION FILTERS

BACKGROUND OF THE INVENTION

The invention relates to an x-ray diagnostic apparatus, comprising positioning means for the shifting of a selected radiation filter of a plurality of radiation filters into the path of an x-ray beam.

An x-ray diagnostic apparatus of this type is described in U.S. Pat. No. 3,976,889. In this x-ray diagnostic apparatus the adaptation of the x-radiation to the respective radiography subject proceeds through shifting of one of a plurality of radiation filters into the radiation path in advance of the radiography subject. The radiation filters are arranged on a rotatably mounted disc whose axis of rotation is offset relative to the central ray of the x-ray beam, said disc being capable of being manually rotated. A parameter which determines the respective filter to be shifted into the ray path is the density of the examination subject. In the case of the known x-ray examination apparatus the operating individual must estimate this density and select the corresponding filter.

SUMMARY OF THE INVENTION

An example of a commercial mammography apparatus is disclosed in a brochure of Siemens AG entitled "MAMMOMAT B," Kompakter Mammographie-Arbeitsplatz, PIR 87-022, M-R 87 7318, January 1982. In this commercial apparatus, the application of compression to the examination subject is accomplished by a motor driven compression plate, the motion of which is controlled by a foot petal. The maximum exertible pressure can be set in a range from 87 newtons per unit of area to 150 newtons per unit of area during assembly.

An x-ray spot film device is described in German OS No. 23 56 276, wherein the speed of the drive motor is switched in steps in dependency upon the force acting on the patient.

The object underlying the invention resides in automating the filter selection and positioning in that the density of the radiography subject is automatically detected and the filter adjustment proceeds correspondingly.

Accordingly, this object is achieved in that means are present for the formation of an electric density signal which is dependent upon the density of the examination subject, and that the adjustment means contains an electromotor activated by a control circuit to which the density signal is supplied and which activates the motor, corresponding to the respective density signal, for the purpose of selection of the respective filter. The invention is particulalry suitable for apparatus for the preparation of mammography exposures where a compression of the respective examined mamma is a necessary part of the procedure. The density signal can be formed from the respective compression force and/or the respective length of the compression path.

The invention will be explained in greater detail in the following on the basis of an exemplary embodiment illustrated on the accompanying drawing sheet; and other objects, features and advantages will be apparent from this detailed disclosure and from the appended claims.

BRIEF DESCRIPTION OF THE DRAWING

The single FIGURE is a diagrammatic illustration of an x-ray diagnostic apparatus embodying a filter selection and positioning system in accordance with the present invention.

DETAILED DESCRIPTION

In the drawing an x-ray diagnostic apparatus for the preparation of mamma radiographs is illustrated including an x-ray source 1 and a support table 2 for the radiography subject 3. Serving the purpose of compression of the radiography subject 3 is a compression device comprising a compression localizer 4 which is mounted on a compression carriage 5 and which is pressed by means of an electromotor 6 against the radiography subject 3. When the localizer engages the radiography subject 3 and attains a specific specified compression force, the motor 6 is shut off. With the compression localizer 4 resting against the radiography subject 3, a spring 7 is tensioned corresponding to the respective compression force, which spring is secured to one end of a lever 8 which is pivotally mounted about a shaft 9, and which, at the other end, supports the compression localizer 4. The spring 7, in conjunction with an actual value transducer 10, forms an electric signal corresponding to the compression force exerted by the localizer 4.

In the illustrated apparatus, in addition, the respective compression path s is detected by a path length transducer 11 and converted into an electric signal. The transducer may be coupled wtih the output drive train driven by motor 6 as indicated by the dash line 11a. The motor 6 (which is secured to carrage 5) positions the carriage 5 via a toothed wheel 12 which has rolling engagement with a fixedly mounted toothed rack 13 which is fixed relative to support table 2.

The actual value signals for the compression force and compression paths are supplied via lines 14a and 15a to inputs 14 and 15 of the density computer 16 which determines therefrom the density of the radiography subject 3 and hence the respectively required radiation filter. A signal corresponding to the required filter is connected to the output 17 of the density computer 16.

The provided radiation filters can be arranged in the manner described in U.S. Pat. No. 3,976,889 on a disc 19 rotatably mounted in an eccentric fashion relative to the central ray of the x-radiation 18. In order to rotate the disc 19 an electromotor 20 is provided which forms an actual value signal on the line 21 which corresponds to the filter respectively shifted into the ray path 18 (in the example a filter 19a is shown in the operating position). This actual value signal on the line 21 is compared with the desired value signal on the line 17. If the filter disposed in the ray path does not agree with the required filter, an amplifier 22 will deliver a signal at its output 23 which switches on the motor 20 until the signals on the lines 17 and 21 correspond.

Instead of the detection of the compression force and of the compression path, in the case of simple apparatus with a fixedly adjusted compression force, it can be sufficient to detect only the respective compression path.

The density signal on the line 17 can also be supplied via an interface to the x-ray high voltage generator supplying the x-ray source 1 and in this fashion an automatic adjustment of the x-ray tube voltage can take place as described, for example, in U.S. Pat. No. 3,991,314.

It will be apparent that many modifications and variations may be made without departing from the scope of the teachings and concepts of the present invention.

We claim as our invention:

1. An x-ray diagnostic apparatus comprising x-ray generator means for supplying x-ray energy along a ray path, a plurality of radiation filters mounted for selective positioning in the ray path, positioning means for shifting one of the plurality of radiation filters into the ray path, density sensing means for forming an electric density signal which is dependent upon the density of a radiography subject disposed in said radiation path, said positioning means including a motor and a control circuit coupled with said density sensing means for controlling said motor such that upon receipt of a density signal from said density sensing means said control circuit activates the motor corresponding to the received density signal for selecting one of said filters suitable to the sensed density.

2. An x-ray diagnostic apparatus according to claim 1, further comprising a compression device for the radiography subject, and wherein said density sensing means comprises a transducer means coupled with the compression device for sensing a measure of the compression of the radiography subject.

3. An x-ray diagnostic apparatus according to claim 1, wherein said patient density sensing means is coupled with said x-ray generator means for automatically adjusting the x-ray tube voltage in accordance with the sensed density.

4. An x-ray diagnostic apparatus according to claim 1, wherein said positioning means comprises a shaft connected to said motor and a disk 19 carrying said plurality of radiation filters, said disk 19 being mounted on said shaft for rotating said filters through said ray path.

* * * * *